United States Patent [19]

Medoff

[11] Patent Number: 5,718,704
[45] Date of Patent: Feb. 17, 1998

[54] L-SHAPE SURGICAL BUTTRESS PLATE

[76] Inventor: Robert J. Medoff, 159 Ku'ukama St., Kailua, Hi. 96734

[21] Appl. No.: 590,921

[22] Filed: Jan. 24, 1996

[30] Foreign Application Priority Data

Feb. 14, 1995 [SE] Sweden .................. 9500566

[51] Int. Cl.⁶ .................. A61B 17/56
[52] U.S. Cl. .................. 606/69; 606/70
[58] Field of Search .................. 606/69, 70, 71

[56] References Cited

U.S. PATENT DOCUMENTS

| 4,565,193 | 1/1986 | Streli | 128/92 D |
| 4,651,724 | 3/1987 | Berentey et al. | 606/69 |
| 5,586,985 | 12/1996 | Putnam et al. | 606/69 |

FOREIGN PATENT DOCUMENTS

| 2405062 | 5/1979 | France . | |
| 2405705 | 5/1979 | France . | |
| 2472373 | 7/1981 | France . | |
| 1827209 | 7/1993 | U.S.S.R. | 609/69 |

*Primary Examiner*—Michael Buiz
*Assistant Examiner*—Julian W. Woo
*Attorney, Agent, or Firm*—Ladas & Parry

[57] ABSTRACT

The present invention relates to an implantable buttress plate (1) for fixation of volar rim fragments (11) at the distal radius (10). The plate (1) is of L-shape with holes (5) in one or both of the legs of the L. The holes (5) are designed for receiving fasteners, e.g. bone screws (6). The plate (1) has a shape adapted to the intended use.

9 Claims, 1 Drawing Sheet

L-SHAPE SURGICAL BUTTRESS PLATE

FIELD OF THE INVENTION

The present invention relates to an implantable buttress plate for fixation of a palmar or volar rim fragment at the distal radius.

BACKGROUND

Frequently, fractures may involve the volar (palmar) portion of the distal radius including the volar rim. In some situations, such as Barton's fracture, this type of fragmentation may be isolated, and contribute to volar (palmar) instability of the wrist as it displaces into the fracture site. In other fracture patterns, such as a comminuted Colles' fracture, volar fragmentation makes open reduction extremely difficult because of the lack of support of this rim. This may require multiple incisions if open reduction is attempted in order to reduce the dorsal fragmentation as well as re-establish a volar buttress for the wrist. This type of extensive soft tissue dissection, however, may further compromise the soft tissues.

Typically, the buttress plate use for the above volar fragments is designed with a "T" type configuration and involves dissection through the midline along the palmar side of the distal forearm. The buttress plate is attached to the proximal fragment; distally, the plate pushes against the rim fragments holding them in position.

The existing "T" buttress plates require a relatively long and extensive palmar exposure, retraction of the median nerve and radial vessels producing relatively extensive bleeding. A further problem with this method is that in the presence of a comminuted Colles' fracture the surgeon is hesitant to have to make incisions from both the dorsal and the palmar side.

SUMMARY OF THE INVENTION

One objective of the present invention is to provide a device circumventing the above drawbacks. This will be attained by means of a buttress plate according to the characterizing part of claim 1.

By using a buttress plate having an "L" type configuration according to the present invention, it is possible to apply the plate using a radial incision, which is less traumatic. The incision is smaller than for the traditional palmar approach.

Further objectives and advantages of the present invention will be apparent from the detailed description below.

BRIEF DESCRIPTION OF THE DRAWING

The present invention will now be described in greater detail hereinbelow, with reference to the embodiments shown in the drawings. In the accompanying drawings.

DETAILED DESCRIPTION OF PREFERRED EMBODIMENT

Figure 1:
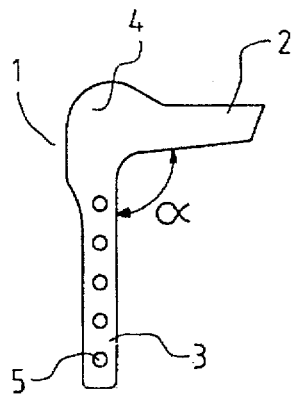
FIG. 1 is a top view of a buttress plate according to the invention.
Figure 2:
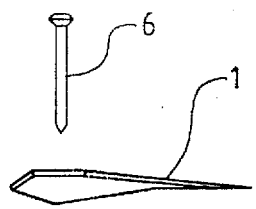
FIGS. 2 and 3 are end and side views, respectively, of the plate of FIG. 1.
Figure 3:
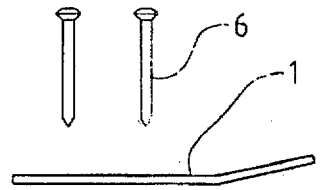

One embodiment according to the invention is shown in FIGS. 1-5. Therein, a buttress plate 1 has a general L-shape in top view. The angle $\alpha$ between the two legs 2,3 of the "L" is approx. 90°. One leg 3 of the plate 1 is furnished with a number of openings 5 for receiving fastening means 6. At the juncture of transition 4 between the two legs 2,3 of the plate 1 an enlarged area is furnished at the outer part of the transition 4. In other embodiments not shown there is no enlarged area. This transition zone 4 is intended for support at the flare of the radial styloid.

Both of the legs 2,3 correspond to the shape of the bone to which the plate 1 is fixed. The angle $\alpha$ between the legs 2,3 may vary from 60° to 115° in different embodiments of the invention. However, an angle $\alpha$ of approx. 75°–110° is the most common.

Figure 5:
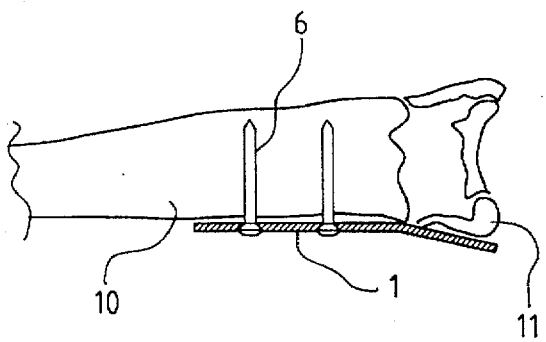
FIGS. 4 and 5 are top and side sectional views, respectively, of the the plate of previous Figures. applied on the radius.
Figure 4:
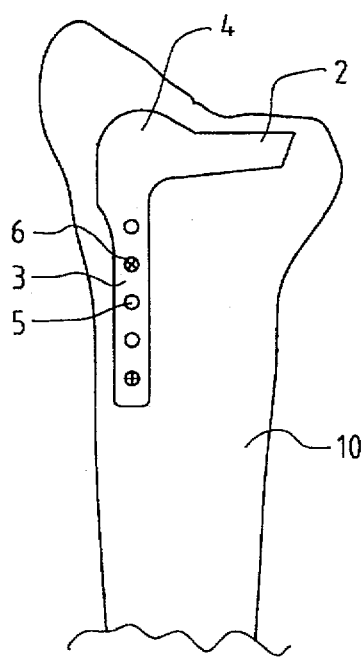

FIGS. 4 and 5 show installation of plate 1 on the radius 10. The L-plate 1 is used in this example as a buttress for a palmar rim fragment 11 at the distal radius. To place the buttress plate 1 a limited incision is made along the radial side of the forearm. The base of the plate is slid up under the palmar soft tissue of the radius 10 to buttress the rim fragment 11.

When the plate 1 is in the desired position it is fixed to the radius 10 by means of suitable fastening means passing through openings 5 in leg 3 of the L-plate 1. In the drawings the fastening means are shown as screws 6. In other embodiments the screws 6 are replaced by pins, wires, blades, staples, brackets or indirect coaption with another device securely attached to the stable bone fragment. Furthermore, a person skilled in the art appreciates that the number of apertures or holes for fixation of the plate 1 is not critical, as long as a stable fixation is achievable.

The leg 2 of the buttress plate 1 intended to support the palmar rim fragment 11 is bent in a shape adapted to the form of the styloid of the radius. Thus, said leg 2 has a curved shape which follows the end of the radius. The other leg 3 of the buttress plate 1 is contoured for the radial side of the lower forearm. This allows a limited incision and makes it much easier for placement of the fastening means.

Figure 6:
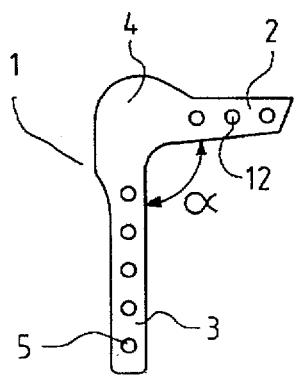
FIG. 6 is a top view of a further embodiment of a buttress plate according to the invention.

The embodiment shown in FIG. 6 corresponds to the embodiment shown in FIGS. 1 to 5 except that holes 12 are provided also in the leg 2 of the buttress plate 1 intended to support the palmar rim fragment 11. This allows the placement of fastening means, e.g. screws, in the part 2 of the plate 1 abutting the volar or palmar rim of the distal radius.

In further embodiments, pointed projections (not shown) are furnished at the ends of the plate. These pointed projections aid in purchasing the fragments that are buttressed, and prevent the fragments from shifting.

The above detailed description has referred to but a limited number of embodiments of the present invention, but it will be readily perceived by a person skilled in the art that the present invention encompasses a large number of embodiments without departing from the spirit and scope of the appended claims.

What is claimed is:

1. An implantable buttress plate (1) for fixation of a palmar or volar rim fragment (11) at the distal radius (10), said plate comprising a plate member of L-shape as viewed from above and wherein said plate member has two legs (2, 3) only one of which (3) is furnished with at least one hole (5) for receiving fastening means (6) for securing the plate member, (1) to a stable bone (10), the other leg (2) being solid without holes, said other leg extending from said one leg a substantial distance to form said L-shape of said plate member and serve as a buttressing means for the palmar or volar rim fragment without attachment thereto by fastening means.

2. The plate of claim 1, wherein said plate member has a transition region at which said legs are connected, said transition region comprising an enlarged area of the plate member (1), as viewed from above, at an outer part of said transition region (4) of the two legs (2, 3) of the L-shape member.

3. The plate of claim 2, wherein said outer part of said enlarged area of said transition region forms a rounded corner for said L-shape plate member.

4. The plate of claim 1, wherein said one of said legs (2) is bent in a shape adapted to the form of the styloid of the radius (10).

5. The plate of claim 1, wherein said plate member is flat and insertable in a single, limited incision along the radial side of the lower forearm.

6. The plate of claim 1, wherein said fastening means are screws (6), pins, wires, blades, staples, brackets or indirect coaption with another device securely attached to the stable bone (10).

7. The plate of claim 1, wherein said two legs (2, 3) form an angle ($\propto$) therebetween of from 60° to 115°.

8. The plate of claim 7, is from 75° to 100°.

9. The plate of claim 1, wherein said one leg is extendable along the radius and the other leg is extendable transversely at the rim fragment, said one leg being longer than the other leg.

* * * * *